(12) United States Patent
Shih et al.

(10) Patent No.: US 8,563,756 B2
(45) Date of Patent: Oct. 22, 2013

(54) METHOD AND APPARATUS FOR PREPARING HYDROXYMETHYLFURFURAL

(75) Inventors: Ruey-Fu Shih, Hsinchu (TW); Hsi-Yen Hsu, Taipei (TW)

(73) Assignee: Industrial Technology Research Institute, Hsinchu County (TW)

( * ) Notice: Subject to any disclaimer, the term of this patent is extended or adjusted under 35 U.S.C. 154(b) by 413 days.

(21) Appl. No.: 12/972,527

(22) Filed: Dec. 20, 2010

(65) Prior Publication Data
US 2012/0016141 A1    Jan. 19, 2012

(30) Foreign Application Priority Data

Jul. 15, 2010    (TW) .................................. 99123241 A

(51) Int. Cl.
*C07D 307/46*    (2006.01)
*B01D 3/40*    (2006.01)

(52) U.S. Cl.
USPC .......................................... 549/488; 422/235

(58) Field of Classification Search
USPC .......................................... 549/488; 422/235
See application file for complete search history.

(56) References Cited

U.S. PATENT DOCUMENTS

| 2,292,823 A | 8/1942 | Dashew |
| 4,590,283 A | 5/1986 | Gaset et al. |
| 7,317,116 B2 | 1/2008 | Sanborn |
| 2008/0033187 A1 | 2/2008 | Zhao et al. |
| 2008/0033188 A1 | 2/2008 | Dumesic et al. |

*Primary Examiner* — Bernard Dentz
(74) *Attorney, Agent, or Firm* — Pai Patent & Trademark Law Firm; Chao-Chang David Paj

(57) ABSTRACT

In an embodiment of the invention, an apparatus for preparing hydroxymethylfurfural (HMF) is provided. The apparatus includes a reaction area including a first organic layer including sugar and a solvent and a second organic layer including a solvent mixture with azeotropy and extractability, a boiling area including a mixing solution formed by the hydroxymethylfurfural and the solvent mixture, connected with the reaction area, and a distilling area including water and a liquid layer including the solvent mixture, connected to the reaction area. In another embodiment of the invention, a method for preparing hydroxymethylfurfural (HMF) is provided.

13 Claims, 1 Drawing Sheet

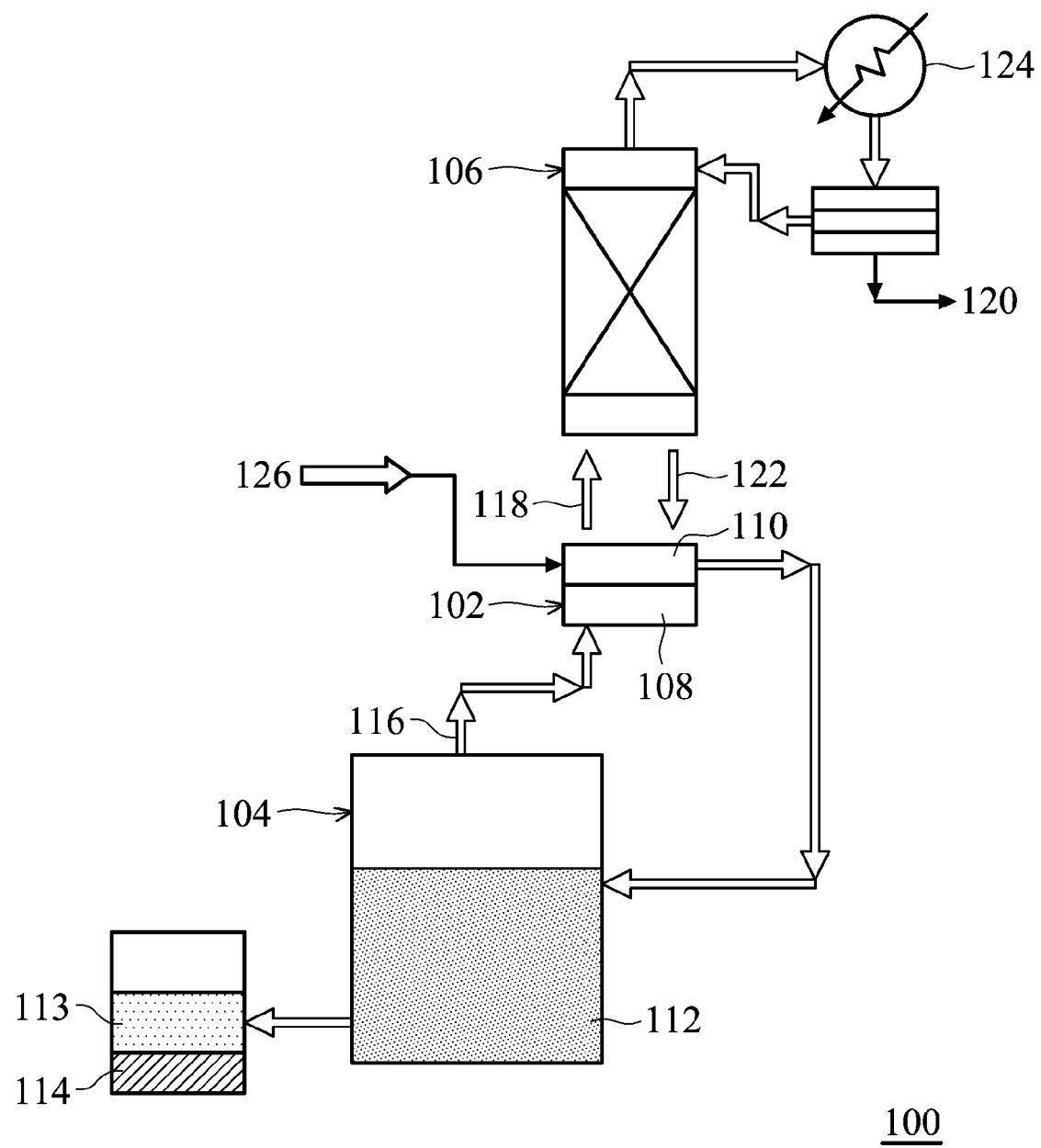

METHOD AND APPARATUS FOR PREPARING HYDROXYMETHYLFURFURAL

CROSS REFERENCE TO RELATED APPLICATIONS

This Application claims priority of Taiwan Patent Application No. 99123241, filed on Jul. 15, 2010, the entirety of which is incorporated by reference herein.

BACKGROUND OF THE INVENTION

1. Field of the Invention

The invention relates to an apparatus for preparing chemicals, and in particular to a method and apparatus for preparing hydroxymethylfurfural (HMF).

2. Description of the Related Art

Oil reserves in the world are gradually being depleted. Meanwhile, the greenhouse effect is continuously growing. Europe, America and Japan have developed a policy, wherein before the year 2020, some materials utilized in plastic consumer products must be derived from renewable resources. Thus, research into using biomass raw materials to refine chemical raw materials has become popular. For the BREW and BIOMASS biomass energy development plan, Europe and the United States designated hydroxymethylfurfural (HMF) and its derivatives, 2,5-Furandicarboxylic acid (FDCA), as an important cyclic building block applied on furanic polyester and furanic polyamide biomass plastic products. The intermediate products of hydroxymethylfurfural (HMF) downstream derivatives comprise chemical intermediate products of tetrahydrofuran, synthetic solvents of enamel or resin solvents and raw materials of organic synthesis, in particular, raw materials of pyrrole and thiophene syntheses. In the future, the raw materials for preparing hydroxymethylfurfural (HMF) will be derived from sugar produced by cellulose bio-hydrolysis business technology, which is expected in 2015.

Hydroxymethylfurfural (HMF) is a kind of furfural compound. Hydroxymethylfurfural (HMF) is prepared merely by chemical methods utilizing hexose conversion but not by bio-fermentation methods due to inhibition on microorganism growth in solutions. However, in such chemical methods, it is difficult to control side reactions and separate hydroxymethylfurfural (HMF), resulting in low reaction efficiency and high costs. Thus, related downstream applications of HMF have yet to be successfully commercialized. The reasons causing low hydroxymethylfurfural (HMF) production efficiency comprise the polymerization of hydroxymethylfurfural (HMF) to form humins under a high temperature and in an acidic condition, hydrolysis of hydroxymethylfurfural (HMF) to form levulinic acid under a high temperature and in acidic aqueous solution, and occurrence of a crossed aldol reaction between hydroxymethylfurfural (HMF) and sugar to form humins under a high temperature.

Lewkowski (ARKIVOC 2001) summarizes four hydroxymethylfurfural (HMF) preparation methods comprising a homogeneous aqueous solution reaction process with a temperature of less than 200° C., a homogeneous aqueous solution reaction process with a temperature exceeding 200° C., an organic solution reaction process, and a two-phase reaction process. In the homogeneous aqueous solution reaction process (less than 200° C.), the yield of hydroxymethylfurfural (HMF) is merely 30%. Also, in another homogeneous aqueous solution reaction process (exceeding 200° C.), the yield of hydroxymethylfurfural (HMF) is merely 58%. The organic solution reaction process prevents hydroxymethylfurfural (HMF) from hydrolyzing to form levulinic acid. Szmant published the method comprising utilizing boron trifluoride ether complexes ($BF_3.Et_2O$) as a catalyst, sugar and dimethyl sulfoxide (DMSO) to prepare hydroxymethylfurfural (HMF) in 1981 (J. Chem. Tech. Biotechnol.). For the method taught by Szmant, that was capable of achieving a yield exceeding 90%, was merely fructose. Further, boron trifluoride ether complexes ($BF_3.Et_2O$) are corrosive, expensive and unable to be reused, such that wastewater may be produced, and it is difficult to separate hydroxymethylfurfural (HMF) from dimethyl sulfoxide (DMSO). Thus, the method cannot be commercialized. Archer-Daniels-Midland Co. (U.S. Pat. No. 7,317,116 B2, 2008) discloses the method comprising utilizing high fructose syrup, N-Methyl-2-Pyrrolidone (NMP) or dimethylacetamide (DMAc) and a solid-state catalyst to prepare hydroxymethylfurfural (HMF). However, it is also difficult to separate hydroxymethylfurfural (HMF) from N-Methyl-2-Pyrrolidone (NMP). In the two-phase reaction process, hydroxymethylfurfural (HMF) is continuously extracted from a water phase containing mineral acids at 177° C. through an organic solvent undissolved with water to improve main product yields. However, provision of large amounts of organic solvents and considerable energy to separate hydroxymethylfurfural (HMF) from a mixing solution containing dilute hydroxymethylfurfural (HMF) is required. Also, corrosiveness exists for the method.

In order to reduce side reactions and further commercialized technology, some well-known chemical companies such as Dupont, Merk & Co, Canon KK, FURCHIM and Roquette, and research institutions such as Battelle and the University of Wisconsin are trying to overcome the technical barrier of a low hydroxymethylfurfural (HMF) yield. For instance, Roquette (U.S. Pat. No. 4,590,283, 1986) discloses the method comprising utilizing 20% fructose, dimethyl sulfoxide (DMSO) and AMBERLIT C200 cation resin as a catalyst for reaction at 80° C. and simultaneously utilizing methyl isobutyl ketone (MIBK) to extract hydroxymethylfurfural (HMF) to prepare hydroxymethylfurfural (HMF). Although its yield achieves 97%, 8 hrs of reaction time is consumed. In particular, methyl isobutyl ketone (MIBK) contains merely 2% of dilute hydroxymethylfurfural (HMF). Thus, recovering large amounts of solvents is required, increasing costs. Additionally, the University of Wisconsin discloses the method comprising adding an organic solvent dissolved with hydroxymethylfurfural (HMF) and undissolved with water to an aqueous phase to form a two-phase reaction to reduce hydroxymethylfurfural (HMF) to contact with water to hydrolyze to form levulinic acid. Although the reaction time thereof is only 3 min, its hydroxymethylfurfural (HMF) yield is merely 75%.

BRIEF SUMMARY OF THE INVENTION

One embodiment of the invention provides an apparatus for preparing hydroxymethylfurfural comprising a reaction area comprising a first organic layer comprising sugar and a solvent and a second organic layer comprising a solvent mixture, wherein hydroxymethylfurfural (HMF) and water are produced from the sugar through dehydration reaction in the first organic layer, and the hydroxymethylfurfural is extracted into the second organic layer through the solvent mixture, a boiling area comprising a mixing solution formed by the hydroxymethylfurfural and the solvent mixture, connected with the reaction area, wherein the mixing solution is boiled to form a first vapor which flows into the reaction area, and the second organic layer in the reaction area is reflowed back into the boiling area, and a distillation area comprising water and a liquid layer having the solvent mixture is connected with the reaction area, wherein water and the first vapor in the reaction area are mixed to form a second vapor which flows into the distillation area, and the liquid layer is reflowed back into the second organic layer in the reaction area.

One embodiment of the invention provides a method for preparing hydroxymethylfurfural comprising preparing a sugar solution comprising sugar and a solvent, conducting the sugar solution into a reaction area to form a first organic layer, boiling a solvent mixture in a boiling area to form a first vapor, which flows into the reaction area to form a second organic layer, producing hydroxymethylfurfural and water from the sugar through dehydration reaction in the first organic layer, wherein the hydroxymethylfurfural is extracted into the second organic layer through the solvent mixture, mixing water and the first vapor in the reaction area to form a second vapor which flows into a distillation area to form water and a liquid layer having the solvent mixture in the distillation area, reflowing the liquid layer into the second organic layer in the reaction area, reflowing the second organic layer in the reaction area into the boiling area to form a mixing solution formed by the hydroxymethylfurfural and the solvent mixture in the boiling area, boiling the mixing solution in the boiling area to form the first vapor, which flows into the reaction area, and cooling the remaining mixing solution in the boiling area to separate a solvent mixture-rich third organic layer from a hydroxymethylfurfural (HMF)-rich fourth organic layer.

In order to improve the yield of the hydroxymethylfurfural (HMF) converted from the hexose through the dehydration reaction, the sugar solution is continuously conducted into the chemical reaction apparatus containing catalysts (the reaction area). In the apparatus, while the hydroxymethylfurfural (HMF) is produced, the main product, hydroxymethylfurfural (HMF), is simultaneously extracted out and the by-product, water, is also removed through azeotropic distillation (the distillation area). Thus, a hydroxymethylfurfural (HMF) with high yield is obtained.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawing, wherein:

FIG. 1 shows a method and apparatus for preparing hydroxymethylfurfural according to an embodiment of the invention.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Referring to FIG. 1, in accordance with an embodiment of the invention, an apparatus for preparing hydroxymethylfurfural is disclosed. An apparatus 100 comprises a reaction area 102, a boiling area 104 and a distillation area 106. The reaction area 102 comprises a first organic layer 108 and a second organic layer 110. The first organic layer 108 comprises sugar, a solvent and a catalyst. The second organic layer 110 comprises a solvent mixture. In the first organic layer 108, hydroxymethylfurfural (HMF) and water are produced from the sugar through dehydration reaction, and the hydroxymethylfurfural (HMF) is extracted into the second organic layer 110 through the solvent mixture. When various solvents are selected, the densities of such organic layers are altered such that the hydroxymethylfurfural (HMF) may be optionally dispersed in the first organic layer or the second organic layer.

The boiling area 104 is connected with the reaction area 102. The boiling area 104 comprises a mixing solution 112 formed by the hydroxymethylfurfural and the solvent mixture. The mixing solution 112 is boiled to form a first vapor 116, which flows into the reaction area 102. The first vapor 116 conducted from the boiling area 104 may serve as a heat source for the dehydration reaction performed in the reaction area 102 to convert the sugar into the hydroxymethylfurfural (HMF). The second organic layer 110 in the reaction area 102 is reflowed back into the boiling area 104. The remaining mixing solution 112 is cooled to separate a solvent mixture-rich third organic layer 113 from a hydroxymethylfurfural (HMF)-rich fourth organic layer 114. When various solvents are selected, the densities of such organic layers are altered such that the hydroxymethylfurfural (HMF) may be optionally dispersed in the third organic layer or the fourth organic layer.

The distillation area 106 is connected with the reaction area 102. The distillation area 106 comprises water and a liquid layer 122 (not shown). The liquid layer comprises the solvent mixture. Water produced from the dehydration reaction and the first vapor 116 in the reaction area 102 are mixed to form a second vapor 118, which flows into the distillation area 106. Water 120 is discharged from the distillation area 106. The liquid layer 122 is reflowed back into the second organic layer 110 in the reaction area 102. The distillation area 106 further comprises a condenser 124 to condense the second vapor 118 to form water 120 and the liquid layer 122.

In the first organic layer 108, the sugar may comprise glucose, sucrose, fructose or high fructose syrup. The solvent may be an aprotic polar solvent, for example, dimethyl sulfoxide (DMSO), dimethylacetamide (DMAc), dimethylformamide (DMF) or N-methyl-2-pyrrolidone (NMP). The catalyst may comprise a solid-state catalyst such as acidic ion exchange resin, zeolite or heteropolyacids (HPA) or homogeneous catalyst such as Lewis acids, ammonium chloride ($NH_4Cl$), organic ammonium chloride, hydrochloric acid metal salt, nitric acid metal salt, phosphoric acid metal salt or sulfuric acid metal salt. When the homogeneous catalyst is selected, it is prepared in the feed. Optionally, when the solid-state catalyst is selected, it is disposed in the reaction area before feeding.

The solvent mixture with azeotropy and extractability may comprise a first solvent, a second solvent or combinations thereof with a specific ratio based on the requirement for azeotropy and extractability. The first solvent (may comprise alkane or chloroalkane, or preferably C7-8 alkane) has difficulty being dissolved with dimethyl sulfoxide (DMSO), dimethylacetamide (DMAc), dimethylformamide (DMF) or N-methyl-2-pyrrolidone (NMP) in the first organic layer 108, and can form a low azeotropic point with water. The second solvent (may comprise ester, ketone, ether or chlorobenzene, or preferably ester or ketone, for example, alkyl acetate (C2-4) ester or C4-6 ketone) does not dissolve with water.

The reaction area 102 may comprise a liquid accumulation area formed by a plurality of distillation plates and the spaces thereamong or one or more flashdrums with a series connection for gas-liquid contact. The distillation area 106 may comprise a plurality of distillation plates or filling layers.

The disclosed apparatus for preparing hydroxymethylfurfural is divided into the boiling area for boiling and evaporating the solvent mixture, the reaction area for performing the dehydration reaction and extracting the hydroxymethylfurfural (HMF) and the distillation area for dehydrating; thus, simultaneously achieving sugar dehydration, hydroxymethylfurfural (HMF) extraction and water removal. The reaction area for performing the dehydration reaction and extracting the hydroxymethylfurfural (HMF) and the distillation area are disposed in a tower. The sugar/solvent is fed into the lower portion (for performing the dehydration reaction and extracting the hydroxymethylfurfural (HMF)) of the tower and contact with the first vapor to perform the dehydration reaction with a balanced temperature of 80-130° C. Two liquid layers are formed due to indissolubility between the sugar/solvent and the second organic layer (the solvent mixture). The hydroxymethylfurfural (HMF) is produced from the sugar through the dehydration reaction and dissolved into the second organic layer. The catalyst is merely in the first organic layer without dissolution into the second organic layer to prevent the hydroxymethylfurfural (HMF) from self-condensation and hydrolysis. An azeotropic vapor (the second vapor) is formed from water produced after the dehydration reaction and the solvent mixture of the first vapor and moved to the upper portion of the tower. After passing through the top of the tower (the distillation area, 104-115° C.) and the condenser, the second vapor is separated into two liquid phases. The upper-layer liquid (the liquid layer) comprises the solvent mixture which is then reflowed back into the reaction area. The lower-layer liquid is a water-rich layer which is then collected by a bottle. In the lower portion of the tower, the second organic layer containing the solvent mixture and the hydroxymethylfurfural (HMF) is conducted into the boiling area. The solvent mixture is re-evaporated to form the first vapor returning to the lower portion of the tower. A high-concentration hydroxymethylfurfural (HMF) resulting solution is formed in the boiling area. After cooling, the resulting solution is separated into a solvent mixture-rich liquid layer and a hydroxymethylfurfural (HMF)-rich liquid layer. The hydroxymethylfurfural (HMF)-rich liquid layer contains hydroxymethylfurfural (HMF) with a concentration of about 90-130 mg/ml.

Still referring to FIG. 1, in accordance with an embodiment of the invention, a method for preparing hydroxymethylfurfural is disclosed. First, a sugar solution 126 is prepared. The sugar solution 126 comprises sugar, a solvent and a catalyst. In an embodiment, some aprotic polar solvents which is capable of dissolving hexose or sucrose, for example, dimethyl sulfoxide (DMSO), dimethylacetamide (DMAc), dimethylformamide (DMF) or N-methyl-2-pyrrolidone (NMP) are utilized to prepare the sugar solution with 1-30 wt %. The sugar solution 126 is conducted into a reaction area 102 to form a first organic layer 108. A solvent mixture is poured into a boiling area 104 to boil to form a first vapor 116, which flows into the reaction area 102 to form a second organic layer 110. Hydroxymethylfurfural (HMF) and water are produced from the sugar through dehydration reaction under the catalyst in the first organic layer 108. The hydroxymethylfurfural (HMF) is extracted into the second organic layer 110 through the solvent mixture. Water produced from the dehydration reaction and the first vapor 116 in the reaction area 102 are mixed to form a second vapor 118 into a distillation area 106 to form water and a liquid layer in the distillation area 106. The liquid layer comprises the solvent mixture. Water 120 discharged from the distillation area 106 is collected. The liquid layer 122 is reflowed back into the second organic layer 110 in the reaction area 102. The second organic layer 110 in the reaction area 102 is reflowed back into the boiling area 104 to form a mixing solution 112 formed by the hydroxymethylfurfural and the solvent mixture in the boiling area 104. The mixing solution 112 is boiled to form the first vapor 116, which flows into the reaction area 102. The remaining mixing solution 112 is collected. After cooling, the mixing solution is separated into a solvent mixture-rich third organic layer 113 and a hydroxymethylfurfural (HMF)-rich fourth organic layer 114.

In the sugar solution 126, the sugar may comprise glucose, sucrose, fructose or high fructose syrup. The solvent may be an aprotic polar solvent, for example, dimethyl sulfoxide (DMSO), dimethylacetamide (DMAc), dimethylformamide (DMF) or N-methyl-2-pyrrolidone (NMP). The catalyst may comprise solid-state catalyst such as acidic ion exchange resin, zeolite or heteropolyacids (HPA) or homogeneous catalyst such as Lewis acids, ammonium chloride ($NH_4Cl$), organic ammonium chloride, hydrochloric acid metal salt, nitric acid metal salt, phosphoric acid metal salt or sulfuric acid metal salt. When the homogeneous catalyst is selected, it is prepared in the feed. Optionally, when the solid-state catalyst is selected, it is disposed in the reaction area.

The solvent mixture with azeotropy and extractability may comprise a first solvent, a second solvent or combinations thereof with a specific ratio based on the requirement for azeotropy and extractability. The first solvent (may comprise alkane or chloroalkane, or preferably C7-8 alkane) has difficulty being dissolved with dimethyl sulfoxide (DMSO), dimethylacetamide (DMAc), dimethylformamide (DMF) or N-methyl-2-pyrrolidone (NMP) in the first organic layer 108, but can form a lowest azeotropic point with water. The second solvent (may comprise ester, ketone, ether or chlorobenzene, or preferably ester or ketone, for example, alkyl acetate (C2-4) ester or C4-6 ketone) does not dissolve with water.

The reaction area 102 may comprise a liquid accumulation area formed by a plurality of distillation plates and the spaces thereamong or one or more flashdrums with a series connection for gas-liquid contact. The distillation area 106 may comprise a plurality of distillation plates or filling layers.

The sugar in the sugar solution 126 has a weight ratio of about 1-30%. In the second organic layer 110, alkane and at least one of ester, ketone, ether, chlorobenzene and chloroalkane of the solvent mixture have a weight ratio of 1:1-1:0, or preferably 1:1-3:1. In an embodiment, when the solvent mixture is free from alkane, chloroalkane and at least one of ester, ketone, ether and chlorobenzene have a weight ratio of 1:1-1:0 in the second organic layer 110. The dehydration reaction is performed at a temperature of 80-150° C. for 10 min to 3 hrs, or preferably for 20 min to 2 hrs. The top of the distillation area 106 has a temperature of about 104-115° C. The ester, ketone, ether or chlorobenzene of the solvent mixture has a weight ratio of about 1:2 with the aprotic polar solvent. The solvent mixture with azeotropy and extractability and the aprotic polar solvent forms a low azeotropic point, facilitating separation of the hydroxymethylfurfural (HMF) therefrom.

In order to improve the yield of the hydroxymethylfurfural (HMF) converted from the hexose through the dehydration reaction, the sugar solution is continuously conducted into the chemical reaction apparatus containing catalysts (the reaction area). In the apparatus, while the hydroxymethylfurfural (HMF) is produced, the main product, hydroxymethylfurfural (HMF), is simultaneously extracted out and the by-product, water, is also removed through azeotropic distillation (the distillation area). Thus, a hydroxymethylfurfural (HMF) with high yield is obtained.

Example 1

Preparation of Hydroxymethylfurfural (HMF) (1)

256 g of n-octane and 125 g of isobutyl acetate were poured into the boiling area to boil. After, the temperature and flow rate of the boiling area, the reaction area and the dehydration distillation area were stable. Meanwhile, a sugar solution containing 20.0 g of fructose, 1.56 g of ammonium chloride ($NH_4Cl$, catalyst) and 80.12 g of dimethyl sulfoxide (DMSO) was continuously conducted into the reaction area with a flow rate of 8.1 ml/min until 10 min 50 sec. At that time, the temperature of the boiling area was 122° C., the temperature of the reaction area was 116° C. and the temperature of the top of the dehydration distillation area was 109° C. The reaction was completed after 31 min. After cooling, the HPLC was analyzed. In the fourth organic layer, the content of the hydroxymethylfurfural (HMF) was 95 mg/ml. In the first organic layer, the content of the hydroxymethylfurfural (HMF) was 101 mg/ml. The fructose conversion rate was 99.4%. Using GC analysis, in the third and second organic layers, the content of the hydroxymethylfurfural (HMF) was nearly zero. The weight of the fourth organic layer was 34.5 g. The weight of the first organic layer was 71.2 g. The final hydroxymethylfurfural (HMF) product was 10.399 g with a yield of 74.6 mol %.

Example 2

Preparation of Hydroxymethylfurfural (HMF) (2)

223 g of n-heptane and 106 g of isobutyl acetate were poured into the boiling area to boil. After, the temperature and flow rate of the boiling area, the reaction area and the dehydration distillation area were stable. Meanwhile, a sugar solution containing 20.2 g of fructose, 1.554 g of ammonium chloride ($NH_4Cl$, catalyst) and 83.69 g of dimethyl sulfoxide (DMSO) was continuously conducted into the reaction area with a flow rate of 8.1 ml/min until 12 min. At that time, the temperature of the boiling area was 103° C., the temperature of the reaction area was 99° C. and the temperature of the top of the dehydration distillation area was 96° C. The reaction was completed after 60 min. After cooling, the HPLC was analyzed. In the fourth organic layer, the content of the hydroxymethylfurfural (HMF) was 55 mg/ml. In the first organic layer, the content of the hydroxymethylfurfural (HMF) was 129 mg/ml. The fructose conversion rate was 99.9%. Using GC analysis, in the third and second organic layers, the content of the hydroxymethylfurfural (HMF) was nearly zero. The weight of the fourth organic layer was 41.8 g. The weight of the first organic layer was 64.5 g. The final hydroxymethylfurfural (HMF) product was 10.323 g with a yield of 73.4 mol %.

Example 3

Preparation of Hydroxymethylfurfural (HMF) (3)

200 g of n-octane and 154 g of isobutyl acetate were poured into the boiling area to boil. After, the temperature and flow rate of the boiling area, the reaction area and the dehydration distillation area were stable. Meanwhile, a sugar solution containing 20.5 g of fructose, 1.10 g of ferric chloride ($FeCl_3$, catalyst) and 80.11 g of dimethyl sulfoxide (DMSO) was continuously conducted into the reaction area with a flow rate of 4.1 ml/min until 20 min 30 sec. At that time, the temperature of the boiling area was 121° C., the temperature of the reaction area was 119° C. and the temperature of the top of the dehydration distillation area was 115° C. The reaction was completed after 45 min. After cooling, the HPLC was analyzed. In the fourth organic layer, the content of the hydroxymethylfurfural (HMF) was 94 mg/ml. In the first organic layer, the content of the hydroxymethylfurfural (HMF) was 69 mg/ml. The fructose conversion rate was 100%. Using GC analysis, in the third and second organic layers, the content of the hydroxymethylfurfural (HMF) was nearly zero. The weight of the fourth organic layer was 77.0 g. The weight of the first organic layer was 56.1 g. The final hydroxymethylfurfural (HMF) product was 10.541 g with a yield of 73.8 mol %.

Example 4

Preparation of Hydroxymethylfurfural (HMF) (4)

228 g of n-octane and 153 g of methyl isobutyl ketone (MIBK) were poured into the boiling area to boil. After, the temperature and flow rate of the boiling area, the reaction area and the dehydration distillation area were stable. Meanwhile, a sugar solution containing 20.0 g of fructose and 80.53 g of dimethyl sulfoxide (DMSO) was continuously conducted into the reaction area containing 8.88 g of Amberlyt-35 (catalyst) with a flow rate of 4.1 ml/min until 19 min 25 sec. At that time, the temperature of the boiling area was 120° C., the temperature of the reaction area was 115° C. and the temperature of the top of the dehydration distillation area was 108° C. The reaction was completed after 42 min. After cooling, the HPLC was analyzed. In the fourth organic layer, the content of the hydroxymethylfurfural (HMF) was 85 mg/ml. In the first organic layer, the content of the hydroxymethylfurfural (HMF) was 39 mg/ml. The fructose conversion rate was 99.4%. Using GC analysis, in the third organic layer, the content of the hydroxymethylfurfural (HMF) was 2.5 mg/ml. In the second organic layer, the content of the hydroxymethylfurfural (HMF) was 0.1 mg/ml. The weight of the fourth organic layer was 80.28 g. The weight of the first organic layer was 81.3 g. The final hydroxymethylfurfural (HMF) product was 10.564 g with a yield of 75.6 mol %.

Example 5

Preparation of Hydroxymethylfurfural (HMF) (5)

294 g of n-octane was poured into the boiling area to boil. After, the temperature and flow rate of the boiling area, the reaction area and the dehydration distillation area were stable. Meanwhile, a sugar solution containing 20.1 g of fructose and 80.31 g of dimethyl sulfoxide (DMSO) was continuously conducted into the reaction area containing 8.9 g of Amberlyt-35 (catalyst) with a flow rate of 5.1 ml/min until 16 min 10 sec. At that time, the temperature of the boiling area was 129° C., the temperature of the reaction area was 123° C. and the temperature of the top of the dehydration distillation area was 117° C. The reaction was completed after 165 min. After cooling, the HPLC was analyzed. In the fourth organic layer, the content of the hydroxymethylfurfural (HMF) was 326 mg/ml. In the first organic layer, the content of the hydroxymethylfurfural (HMF) was 120 mg/ml. The fructose conversion rate was 100%. Using GC analysis, in the third and second organic layers, the content of the hydroxymethylfurfural (HMF) was nearly zero. The weight of the fourth organic layer was 80.29 g. The weight of the first organic layer was 77.31 g. The final hydroxymethylfurfural (HMF) product was 11.493 g with a yield of 82.3 mol %.

Example 6

Preparation of Hydroxymethylfurfural (HMF) (6)

225 g of n-octane and 154 g of isobutyl acetate were poured into the boiling area to boil. After, the temperature and flow rate of the boiling area, the reaction area and the dehydration distillation area were stable. Meanwhile, a sugar solution containing 20.0 g of fructose and 79.96 g of dimethyl sulfoxide (DMSO) was continuously conducted into the reaction area containing 8.84 g of Amberlyt-35 (catalyst) with a flow rate of 5.1 ml/min until 20 min 15 sec. At that time, the temperature of the boiling area was 122° C., the temperature of the reaction area was 118° C. and the temperature of the top of the dehydration distillation area was 108° C. The reaction was completed after 60 min. After cooling, the HPLC was analyzed. In the fourth organic layer, the content of the hydroxymethylfurfural (HMF) was 81 mg/ml. In the first organic layer, the content of the hydroxymethylfurfural (HMF) was 52 mg/ml. The fructose conversion rate was 100%. Using GC analysis, in the third and second organic layers, the content of the hydroxymethylfurfural (HMF) was nearly zero. The weight of the fourth organic layer was 92.7 g. The weight of the first organic layer was 56.7 g. The final hydroxymethylfurfural (HMF) product was 9.856 g with a yield of 70.7 mol %.

Example 7

Preparation of Hydroxymethylfurfural (HMF) (7)

365 g of n-octane was poured into the boiling area to boil. After, the temperature and flow rate of the boiling area, the reaction area and the dehydration distillation area were stable. Meanwhile, a sugar solution containing 20.1 g of fructose and 76.98 g of dimethylacetamide (DMAc) was continuously conducted into the reaction area containing 8.95 g of Amberlyt-35 (catalyst) with a flow rate of 8.1 ml/min until 11 min 40 sec. At that time, the temperature of the boiling area was 127° C., the temperature of the reaction area was 122° C. and the temperature of the top of the dehydration distillation area was 119° C. The reaction was completed after 51 min. After cooling, the HPLC was analyzed. In the fourth organic layer, the content of the hydroxymethylfurfural (HMF) was 118 mg/ml. In the first organic layer, the content of the hydroxymethylfurfural (HMF) was 58 mg/ml. The fructose conversion rate was 100%. Using GC analysis, in the third and second organic layers, the content of the hydroxymethylfurfural (HMF) was nearly zero. The weight of the fourth organic layer was 49.8 g. The weight of the first organic layer was 46.2 g. The final hydroxymethylfurfural (HMF) product was 8.628 g with a yield of 61.7 mol %.

Example 8

Preparation of Hydroxymethylfurfural (HMF) (8)

235.07 g of n-octane and 115.9 g of isobutyl acetate were poured into the boiling area to boil. After, the temperature and flow rate of the boiling area, the reaction area and the dehydration distillation area were stable. Meanwhile, a sugar solution containing 20.08 g of fructose and 80.88 g of dimethyl sulfoxide (DMSO) was continuously conducted into the reaction area containing 8.88 g of DOWEX 50WX8-100 (catalyst) with a flow rate of 4.1 ml/min until 20 min. At that time, the temperature of the boiling area was 122° C., the temperature of the reaction area was 119° C. and the temperature of the top of the dehydration distillation area was 111° C. The reaction was completed after 60 min. After cooling, the HPLC was analyzed. In the fourth organic layer, the content of the hydroxymethylfurfural (HMF) was 102.6 mg/ml. In the first organic layer, the content of the hydroxymethylfurfural (HMF) was 57.5 mg/ml. The fructose conversion rate was 100%. Using GC analysis, in the third and second organic layers, the content of the hydroxymethylfurfural (HMF) was nearly zero. The weight of the fourth organic layer was 74.2 g. The weight of the first organic layer was 74.9 g. The final hydroxymethylfurfural (HMF) product was 11.0 g with a yield of 78.7 mol %.

Example 9

Preparation of Hydroxymethylfurfural (HMF) (9)

235.06 g of n-octane and 116.67 g of isobutyl acetate were poured into the boiling area to boil. After, the temperature and flow rate of the boiling area, the reaction area and the dehydration distillation area were stable. Meanwhile, a sugar solution containing 19.97 g of fructose and 80.21 g of dimethyl sulfoxide (DMSO) was continuously conducted into the reaction area containing 8.92 g of HPA-DW ($H_3W_{12}O_{40}$) (catalyst) with a flow rate of 4.1 ml/min until 20 min. At that time, the temperature of the boiling area was 120° C., the temperature of the reaction area was 115° C. and the temperature of the top of the dehydration distillation area was 105° C. The reaction was completed after 50 min. After cooling, the HPLC was analyzed. In the fourth organic layer, the content of the hydroxymethylfurfural (HMF) was 94.6 mg/ml. In the first organic layer, the content of the hydroxymethylfurfural (HMF) was 52.6 mg/ml. The fructose conversion rate was 100%. Using GC analysis, in the third and second organic layers, the content of the hydroxymethylfurfural (HMF) was nearly zero. The weight of the fourth organic layer was 75.8 g. The weight of the first organic layer was 77 g. The final hydroxymethylfurfural (HMF) product was 10.23 g with a yield of 73.6 mol %.

Example 10

Preparation of Hydroxymethylfurfural (HMF) (10)

237.63 g of n-octane and 115.6 g of isobutyl acetate were poured into the boiling area to boil. After, the temperature and flow rate of the boiling area, the reaction area and the dehydration distillation area were stable. Meanwhile, a sugar solution containing 20.06 g of fructose and 80.57 g of dimethyl sulfoxide (DMSO) was continuously conducted into the reaction area containing 8.93 g of CS-HPA-PW (catalyst) with a flow rate of 4.1 ml/min until 20 min. At that time, the temperature of the boiling area was 121° C., the temperature of the reaction area was 116° C. and the temperature of the top of the dehydration distillation area was 107° C. The reaction was completed after 70 min. After cooling, the HPLC was analyzed. In the fourth organic layer, the content of the hydroxymethylfurfural (HMF) was 80.4 mg/ml. In the first organic layer, the content of the hydroxymethylfurfural (HMF) was 50.4 mg/ml. The fructose conversion rate was 100%. Using GC analysis, in the third and second organic layers, the content of the hydroxymethylfurfural (HMF) was nearly zero. The weight of the fourth organic layer was 83.57 g. The weight of the first organic layer was 74.3 g. The final hydroxymethylfurfural (HMF) product was 9.676 g with a yield of 69.3 mol %.

Example 11

Preparation of Hydroxymethylfurfural (HMF) (11)

236.4 g of n-octane and 115.9 g of isobutyl acetate were poured into the boiling area to boil. After, the temperature and flow rate of the boiling area, the reaction area and the dehydration distillation area were stable. Meanwhile, a sugar solution containing 20.00 g of fructose and 80.23 g of dimethyl sulfoxide (DMSO) was continuously conducted into the reaction area containing 9.55 g of MSR (catalyst) with a flow rate of 4.1 ml/min until 20 min. At that time, the temperature of the boiling area was 122° C., the temperature of the reaction area was 116° C. and the temperature of the top of the dehydration distillation area was 111° C. The reaction was completed after 70 min. After cooling, the HPLC was analyzed. In the fourth organic layer, the content of the hydroxymethylfurfural (HMF) was 80.4 mg/ml. In the first organic layer, the content of the hydroxymethylfurfural (HMF) was 50.4 mg/ml. The fructose conversion rate was 100%. Using GC analysis, in the third and second organic layers, the content of the hydroxymethylfurfural (HMF) was nearly zero. The weight of the fourth organic layer was 86.55 g. The weight of the first organic layer was 89.49 g. The final hydroxymethylfurfural (HMF) product was 10.03 g with a yield of 72.1 mol %.

Example 12

Preparation of Hydroxymethylfurfural (HMF) (12)

235.95 g of n-octane and 115.66 g of diisopropylether were poured into the boiling area to boil. After, the temperature and flow rate of the boiling area, the reaction area and the dehydration distillation area were stable. Meanwhile, a sugar solution containing 20.11 g of fructose and 82.2 g of dimethyl sulfoxide (DMSO) was continuously conducted into the reaction area containing 8.84 g of Amberlyt-35 (catalyst) with a flow rate of 5.1 ml/min until 20 min 15 sec. At that time, the temperature of the boiling area was 116° C., the temperature of the reaction area was 93° C. and the temperature of the top of the dehydration distillation area was 67° C. The reaction was completed after 70 min. After cooling, the HPLC was analyzed. In the fourth organic layer, the content of the hydroxymethylfurfural (HMF) was 162 mg/ml. In the first organic layer, the content of the hydroxymethylfurfural (HMF) was 64 mg/ml. The fructose conversion rate was 100%. Using GC analysis, in the third and second organic layers, the content of the hydroxymethylfurfural (HMF) was nearly zero. The weight of the fourth organic layer was 13.8 g. The weight of the first organic layer was 121 g. The final hydroxymethylfurfural (HMF) product was 8.967 g with a yield of 64.1 mol %.

Example 13

Preparation of Hydroxymethylfurfural (HMF) (13)

237 g of n-octane was poured into the boiling area to boil. After, the temperature and flow rate of the boiling area, the reaction area and the dehydration distillation area were stable. Meanwhile, a sugar solution containing 20.15 g of sucrose, 5 g of water and 75.05 g of dimethyl sulfoxide (DMSO) was continuously conducted into the reaction area containing 8.84 g of Amberlyt-35 (catalyst) with a flow rate of 5.1 ml/min until 23 min. At that time, the temperature of the boiling area was 129° C., the temperature of the reaction area was 122° C. and the temperature of the top of the dehydration distillation area was 117° C. Within 40 min, the water in the tower top was completely reflowed back to provide water to the hydrolyze sucrose. The water layer in a tower-top phase separator was then discharged. The reaction was completed after 100 min. After cooling, the HPLC was analyzed. In the fourth organic layer, the content of the hydroxymethylfurfural (HMF) was 139 mg/ml. In the first organic layer, the content of the hydroxymethylfurfural (HMF) was 139 mg/ml. The sucrose conversion rate was 100%. Using GC analysis, in the third and second organic layers, the content of the hydroxymethylfurfural (HMF) was nearly zero. The weight of the fourth organic layer was 2.4 g. The weight of the first organic layer was 147.78 g. The final hydroxymethylfurfural (HMF) product was 4.977 g with a yield of 35.3 mol %.

Example 14

Preparation of Hydroxymethylfurfural (HMF) (14)

239.9 g of n-octane was poured into the boiling area to boil. After, the temperature and flow rate of the boiling area, the reaction area and the dehydration distillation area were stable. Meanwhile, a sugar solution containing 30.85 g of high fructose syrup (75% sugar (90% fructose, 5% glucose and 5% reducing sugar) and 25% water), 1.65 g of ferric chloride ($FeCl_3$, catalyst) and 70.62 g of dimethylacetamide (DMAc) was continuously conducted into the reaction area with a flow rate of 4.1 ml/min until 23 min 15 sec. At that time, the temperature of the boiling area was 122° C., the temperature of the reaction area was 118° C. and the temperature of the top of the dehydration distillation area was 115° C. The reaction was completed after 60 min. After cooling, the HPLC was analyzed. In the fourth organic layer, the content of the hydroxymethylfurfural (HMF) was 140 mg/ml. In the first organic layer, the content of the hydroxymethylfurfural (HMF) was 58.8 mg/ml. The high fructose syrup conversion rate was 100%. Using GC analysis, in the third and second organic layers, the content of the hydroxymethylfurfural (HMF) was nearly zero. The weight of the fourth organic layer was 26.45 g. The weight of the first organic layer was 66.58 g. The final hydroxymethylfurfural (HMF) product was 7.494 g with a yield of 51.4 mol %.

Example 15

Preparation of Hydroxymethylfurfural (HMF) (15)

248.26 g of n-octane was poured into the boiling area to boil. After, the temperature and flow rate of the boiling area, the reaction area and the dehydration distillation area were stable. Meanwhile, a sugar solution containing 20.077 g of fructose and 81.122 g of dimethyl sulfoxide (DMSO) was continuously conducted into the reaction area containing 8.975 g of DOWEX 50WX8-100 (catalyst) with a flow rate of 4.1 ml/min until 20 min. 126 g of methyl isobutyl ketone (MIBK) was conducted into the reaction area with a flow rate of 4.1 ml/min. At that time, the temperature of the boiling area was 122° C., the temperature of the reaction area was 117° C. and the temperature of the top of the dehydration distillation area was 108° C. The reaction was completed after 60 min. After cooling, the HPLC was analyzed. In the fourth organic layer, the content of the hydroxymethylfurfural (HMF) was 93 mg/ml. In the first organic layer, the content of the hydroxymethylfurfural (HMF) was 73.2 mg/ml. The fructose conversion rate was 99.9%. Using GC analysis, in the third organic layer, the content of the hydroxymethylfurfural (HMF) was 0.15 mg/ml. In second organic layer, the content of the hydroxymethylfurfural (HMF) was nearly zero. The weight of the fourth organic layer was 77.09 g. The weight of the first organic layer was 60.995 g. The final hydroxymethylfurfural (HMF) product was 11.309 g with a yield of 81 mol %.

Example 16

Preparation of Hydroxymethylfurfural (HMF) (16)

279 g of n-octane was poured into the boiling area to boil. After, the temperature and flow rate of the boiling area, the reaction area and the dehydration distillation area were stable. Meanwhile, a sugar solution containing 10.004 g of glucose, 0.440 g of chromium(II) chloride ($CrCl_2$, catalyst) and 91.285 g of dimethylacetamide (DMAc) was continuously conducted into the reaction area with a flow rate of 4.1 ml/min until 22 min. At that time, the temperature of the boiling area was 127° C., the temperature of the reaction area was 124° C. and the temperature of the top of the dehydration distillation area was 108° C. The reaction was completed after 60 min. After cooling, the HPLC was analyzed. In the fourth organic layer, the content of the hydroxymethylfurfural (HMF) was 33.7 mg/ml. In the first organic layer, the content of the hydroxymethylfurfural (HMF) was 10.1 mg/ml. The glucose conversion rate was 98.4%. Using GC analysis, in the third and second organic layers, the content of the hydroxymethylfurfural (HMF) was nearly zero. The weight of the fourth organic layer was 75.24 g. The weight of the first organic layer was 19.46 g. The final hydroxymethylfurfural (HMF) product was 2.907 g with a yield of 41.5 mol %.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An apparatus for preparing hydroxymethylfurfural, comprising:
   a reaction area comprising a first organic layer comprising sugar and a solvent and a second organic layer comprising a solvent mixture, wherein hydroxymethylfurfural (HMF) and water are produced from the sugar through dehydration reaction in the first organic layer, and the hydroxymethylfurfural is extracted into the second organic layer through the solvent mixture;
   a boiling area comprising a mixing solution formed by the hydroxymethylfurfural and the solvent mixture, connected with the reaction area, wherein the mixing solution is boiled to form a first vapor, which flows into the reaction area, and the second organic layer in the reaction area is reflowed back into the boiling area; and
   a distillation area comprising water and a liquid layer having the solvent mixture, connected with the reaction area, wherein water and the first vapor in the reaction area are mixed to form a second vapor which flows into the distillation area, and the liquid layer is reflowed back into the second organic layer in the reaction area.

2. The apparatus for preparing hydroxymethylfurfural as claimed in claim 1, wherein the solvent is an aprotic polar solvent.

3. The apparatus for preparing hydroxymethylfurfural as claimed in claim 1, wherein the solvent mixture comprises alkane, chloroalkane, ester, ketone, ether, chlorobenzene or combinations thereof.

4. The apparatus for preparing hydroxymethylfurfural as claimed in claim 3, wherein alkane comprises C7-C8 alkane.

5. The apparatus for preparing hydroxymethylfurfural as claimed in claim 1, wherein the reaction area comprises a liquid accumulation area formed by a plurality of distillation plates and the spaces thereamong or one or more flashdrums with a series connection for gas-liquid contact.

6. A method for preparing hydroxymethylfurfural, comprising:
   preparing a sugar solution comprising sugar and a solvent;
   conducting the sugar solution into a reaction area to form a first organic layer;
   boiling a solvent mixture in a boiling area to form a first vapor, which flows into the reaction area to form a second organic layer;
   producing hydroxymethylfurfural and water from the sugar through dehydration reaction in the first organic layer, wherein the hydroxymethylfurfural is extracted into the second organic layer through the solvent mixture;
   mixing water and the first vapor in the reaction area to form a second vapor which flows into a distillation area to form water and a liquid layer having the solvent mixture in the distillation area;
   reflowing the liquid layer into the second organic layer in the reaction area;
   reflowing the second organic layer in the reaction area into the boiling area to form a mixing solution formed by the hydroxymethylfurfural and the solvent mixture in the boiling area;
   boiling the mixing solution in the boiling area to form the first vapor, which flows into the reaction area; and
   cooling the remaining mixing solution in the boiling area to separate a solvent mixture-rich third organic layer from a hydroxymethylfurfural (HMF)-rich fourth organic layer.

7. The method for preparing hydroxymethylfurfural as claimed in claim 6, wherein the sugar has a weight ratio of 1-30% in the sugar solution.

8. The method for preparing hydroxymethylfurfural as claimed in claim 6, wherein the solvent mixture comprises alkane, chloroalkane, ester, ketone, ether, chlorobenzene or combinations thereof.

9. The method for preparing hydroxymethylfurfural as claimed in claim 8, wherein when the solvent mixture is free from alkane, chloroalkane and at least one of ester, ketone, ether and chlorobenzene have a weight ratio of 1:1-1:0 in the second organic layer.

10. The method for preparing hydroxymethylfurfural as claimed in claim 8, wherein alkane and at least one of ester, ketone, ether, chlorobenzene and chloroalkane of the solvent mixture have a weight ratio of 1:1-1:0 in the second organic layer.

11. The method for preparing hydroxymethylfurfural as claimed in claim 8, wherein alkane and at least one of ester, ketone, ether, chlorobenzene and chloroalkane of the solvent mixture have a weight ratio of 1:1-3:1 in the second organic layer.

12. The method for preparing hydroxymethylfurfural as claimed in claim 6, wherein the dehydration reaction is performed at a temperature of 80-150° C.

13. The method for preparing hydroxymethylfurfural as claimed in claim 6, wherein the dehydration reaction is performed for 10 min to 3 hrs.

* * * * *